United States Patent
Lee et al.

(10) Patent No.: US 11,802,248 B2
(45) Date of Patent: Oct. 31, 2023

(54) PROCESS FOR REDUCING UNSATURATED HYDROCARBONS IN AROMATIC FRACTION THROUGH SELECTIVE HYDROGENATION

(71) Applicants: SK Innovation Co., Ltd., Seoul (KR); SK Geo Centric Co., Ltd., Seoul (KR)

(72) Inventors: Sang Il Lee, Daejeon (KR); Ji Hoon Lee, Daejeon (KR); Young Eun Cheon, Daejeon (KR)

(73) Assignees: SK Innovation Co., Ltd., Seoul (KR); SK Geo Centric Co., Ltd., Seoul (KR)

( * ) Notice: Subject to any disclaimer, the term of this patent is extended or adjusted under 35 U.S.C. 154(b) by 0 days.

(21) Appl. No.: 17/460,843

(22) Filed: Aug. 30, 2021

(65) Prior Publication Data
US 2022/0073440 A1  Mar. 10, 2022

(30) Foreign Application Priority Data
Sep. 7, 2020 (KR) ........................ 10-2020-0113719

(51) Int. Cl.
*C10G 45/38* (2006.01)
*C07C 7/163* (2006.01)
(Continued)

(52) U.S. Cl.
CPC ............ *C10G 45/38* (2013.01); *B01J 19/245* (2013.01); *B01J 23/28* (2013.01); *B01J 23/882* (2013.01); *B01J 23/883* (2013.01); *B01J 37/18* (2013.01); *B01J 37/20* (2013.01); *C07C 5/03* (2013.01); *C07C 7/163* (2013.01); *C10G 45/08* (2013.01);
(Continued)

(58) Field of Classification Search
CPC ..................................................... C07C 7/163
See application file for complete search history.

(56) References Cited

U.S. PATENT DOCUMENTS 3,228,993 A  *  1/1966  Kozlowski ............. B01J 23/883
                                                         208/143
3,702,291 A  * 11/1972  Jacquin et al. ........ C10G 65/06
                                                         208/143
(Continued)

FOREIGN PATENT DOCUMENTS

FR          3054558 A1  *  2/2018

OTHER PUBLICATIONS

Machine translation FR 3054558. obtained Jun. 9, 2022 (Year: 2022).*

(Continued)

*Primary Examiner* — In Suk C Bullock
*Assistant Examiner* — Alyssa L Cepluch
(74) *Attorney, Agent, or Firm* — THE WEBB LAW FIRM

(57) ABSTRACT

Disclosed are a process and system that are capable of performing selective hydrogenation on aromatic fractions by configuring a catalyst bed through staged loading of a plurality of hydrogenation catalysts with different catalytic properties, or configuring a catalyst system in which a plurality of hydrogenation catalysts are arranged using a plurality of reactors in such a way as to be equivalent with the staged loading, and as a result, are capable of suppressing aromatic loss while improving the selective removal of unsaturated hydrocarbons in the aromatic fraction and durability compared to the case of using a single catalyst.

19 Claims, 4 Drawing Sheets

(51) Int. Cl.
  *C07C 5/03* (2006.01)
  *B01J 19/24* (2006.01)
  *B01J 23/882* (2006.01)
  *B01J 23/28* (2006.01)
  *B01J 23/883* (2006.01)
  *B01J 37/18* (2006.01)
  *B01J 37/20* (2006.01)
  *C10G 45/08* (2006.01)
  *C10G 45/36* (2006.01)
  *C10G 45/40* (2006.01)

(52) U.S. Cl.
  CPC ............ *C10G 45/36* (2013.01); *C10G 45/40* (2013.01); *B01J 2219/0004* (2013.01); *C07C 2523/28* (2013.01); *C07C 2523/882* (2013.01); *C07C 2523/883* (2013.01)

(56) References Cited

U.S. PATENT DOCUMENTS

| | | | |
|---|---|---|---|
| 6,124,514 A * | 9/2000 | Emmrich | C10G 7/08 208/143 |
| 6,284,128 B1 * | 9/2001 | Glover | C10G 69/08 208/143 |
| 2015/0247098 A1 * | 9/2015 | Li | B01J 8/009 585/258 |

OTHER PUBLICATIONS

Inoguchi et al. Study on the Hydrodesulfurization Catalyst of a Residual Fuel (Part 1). Bulletin of the Japan Petroleum Institute. vol. 13, No. 1, May 1971 (Year: 1971).*

* cited by examiner

PROCESS FOR REDUCING UNSATURATED HYDROCARBONS IN AROMATIC FRACTION THROUGH SELECTIVE HYDROGENATION

CROSS-REFERENCE TO RELATED APPLICATION

This application claims priority to Korean Patent Application No. 10-2020-0113719 filed Sep. 7, 2020, the disclosure of which is hereby incorporated by reference in its entirety.

BACKGROUND OF THE INVENTION

Field of the Invention

The present disclosure relates to a process for reducing unsaturated hydrocarbons in an aromatic fraction through selective hydrogenation. More particularly, the present disclosure relates to a process and system that are capable of performing selective hydrogenation on the aromatic fractions by configuring a catalyst bed through staged loading of a plurality of hydrogenation catalysts with different catalytic properties, or configuring a catalyst system in which a plurality of hydrogenation catalysts are arranged using a plurality of reactors in such a way as to be equivalent with the staged loading, and as a result, are capable of suppressing aromatic loss while improving the selective removal of unsaturated hydrocarbons in the aromatic fraction and durability compared to the case of using a single catalyst.

Description of the Related Art

C6+ aromatic hydrocarbons, particularly benzene, toluene, or mixed xylenes (or xylene isomers), account for a large portion of sources for basic chemicals used in the petrochemical field. Benzene or toluene is mainly used as a solvent, fiber, disinfectant, pesticide, pharmaceutical intermediate, dye, pigment, or the like. Mixed xylenes typically include meta-xylene (m-xylene), para-xylene (p-xylene), and ortho-xylene (o-xylene). Among them, p-xylene is a raw material for the synthesis of terephthalic acid, which is used for manufacturing synthetic fabric fibers and resins, and o-xylene serves as a raw material for producing phthalic anhydride. Further, m-xylene is used in plasticizers, azo dyes, etc. Similar boiling points among the xylene isomers make it difficult to separate a particular xylene isomer from mixed xylenes by typical distillation. Instead, adsorption separation, crystallization, and isomerization are mainly employed for the separation and recovery of individual xylenes.

Commercial production of benzene, toluene or mixed xylenes is typically achieved by separation and recovery from aromatic-hydrocarbon-rich fractions or by synthesis through reactions.

Representative of the separation and recovery, among the methods described above, are the method in which mixed xylenes are separated through distillation of reformates obtained by catalytic reforming of naphtha and the method in which mixed xylenes are separated from pyrolysis oil generated as byproducts upon thermal cracking of naphtha.

In recent years, there has been growing interest in the use of zeolite-based catalysts for converting aromatic hydrocarbons (aromatic hydrocarbons including benzene, toluene, and/or C9+ aromatics) to C8 aromatic hydrocarbons, because only limited amounts of xylene can be produced through the conventional processes such as catalytic reforming.

However, aromatic hydrocarbon fractions such as thermal cracking oils as well as reformates contain small amounts of unsaturated hydrocarbons, such as olefins, acetylene, and/or styrene or its derivatives. These unsaturated hydrocarbons deteriorate the performance of the adsorption separation process for separating products or lower the purity of the product because they are difficult to separate using only distillation, which belongs to the common separation technique.

In an attempt to solve the above-described problems, the clay pretreatment or hydrogenation has been performed for reducing the content of olefins in the aromatic hydrocarbon fractions, which would serve as a feedstock of the downstream process, in advance.

As for the clay treatment, clay having acid characteristics can be used as an alkylation catalyst to induce dimerization or trimerization, or aromatic hydrocarbons are converted through alkylation to heavy aromatics and are thus removed as high boiling point fractions that are easy to separate, and thus the method has been widely commercialized. However, the clay is deactivated within a relatively short time in the course of removing olefins in the aromatic fractions, and thus may cause problems related to the process inefficiencies and increased costs due to frequent clay replacement and the generation of solid wastes.

On the other hand, in the case of hydrogenation, hydrogen is supplied in the presence of a catalyst to remove unsaturated hydrocarbons (i.e., olefins, acetylenes, and/or styrene (or its derivatives)) in the aromatic fraction by converting the unsaturated hydrocarbons to saturated hydrocarbons (i.e., paraffins), so that the problems of frequent replacement cycle caused by the clay treatment can be alleviated and the cost of clay and waste generation can be reduced.

Recently, processes for removing unsaturated hydrocarbons from an aromatic fraction have been commercialized by major companies. For example, olefin reduction unit (ORU) technology from UOP, Olgone™ technology from ExxonMobil and Axens, and Arofining technology are known. In particular, selective hydrogenation uses nickel-based catalysts, noble metal-based catalysts (Pt, Pd, etc.), cobalt-molybdenum (Co—Mo), and nickel-molybdenum (Ni—Mo), known in the art as the conventional hydrogenation catalysts.

However, the hydrogenation requires selective saturation of only unsaturated hydrocarbons (e.g., having at least one double-bonded hydrocarbon or triple-bonded hydrocarbon) while minimizing aromatic loss. However, each of the aforementioned catalysts causes great loss of aromatics (that is, aromatic rings as well as unsaturated hydrocarbon are saturated), or, despite the desirable removal rate of unsaturated hydrocarbons, exhibits low durability (the ability to maintain catalytic activity upon long-term operation).

Accordingly, there is a need for improvements in the removal rate of unsaturated hydrocarbons in aromatic fractions and durability while minimizing aromatic loss.

SUMMARY OF THE INVENTION

The present disclosure provides a catalyst system for removing unsaturated hydrocarbons present in an aromatic hydrocarbon fraction through selective hydrogenation, which is capable of suppressing aromatic loss and maintaining good hydrogenation activity even during long-term operation.

In accordance with a first aspect of the present disclosure, it is provided a method of removing unsaturated hydrocarbons in an aromatic fraction, which comprises:
a) providing an aromatic hydrocarbon-containing feedstock having a bromine index of at least 30, and
b) bringing the feedstock into contact with a multi-stage catalyst bed comprising at least one first catalyst bed and a second catalyst bed disposed downstream of the first catalyst bed in a reactor and performing hydrogenation under supply of hydrogen to form an aromatic hydrocarbon-containing product having a reduced bromine index,
wherein,
the first catalyst bed comprises a support containing inorganic oxide, and at least one active metal selected from the group consisting of Ni, Pd, Pt, Ru, Re, Co, Mo, Co—Mo, Ni—Mo, and Ni—W, in which, among the active metals, each of Re, Co, Mo, and Co—Mo is a reduced or sulfide form, and each of Ni, Pd, Pt, Ru, Ni—Mo and Ni—W is a sulfide form, and
the second catalyst bed comprises a support containing inorganic oxide, and Ni—Mo and/or Ni—W in a reduced form as an active metal.

In accordance with a second aspect of the present disclosure, there is provided a method of removing unsaturated hydrocarbons in an aromatic fraction, which comprises:
a) providing an aromatic hydrocarbon-containing feedstock having a bromine index of at least 30, and
b) transferring the feedstock to a multi-stage hydrogenation unit comprising a first reaction unit containing at least one first catalyst and a second reaction unit containing a second catalyst and communicating with the first reaction unit at the downstream of the first reaction unit and performing hydrogenation under supply of hydrogen to form an aromatic hydrocarbon-containing product having a reduced bromine index,
wherein,
the first catalyst comprises a support containing inorganic oxide, and at least one active metal selected from the group consisting of Ni, Pd, Pt, Ru, Re, Co, Mo, Co—Mo, Ni—Mo, and Ni—W, in which, among the active metals, each of Re, Co, Mo, and Co—Mo is a reduced or sulfide form, and each of Ni, Pd, Pt, Ru, Ni—Mo and Ni—W is a sulfide form, and
the second catalyst comprises a support containing inorganic oxide, and Ni—Mo and/or Ni—W in a reduced form as an active metal.

According to an exemplary embodiment, at least 30% by weight of unsaturated hydrocarbons in the aromatic hydrocarbon-containing feedstock may be removed through hydrogenation.

According to an exemplary embodiment, the aromatic loss in the aromatic hydrocarbon-containing product may be less than 1% by weight relative to the aromatic-hydrocarbon-containing feedstock.

According to an exemplary embodiment, the aromatic hydrocarbon-containing feedstock may be a C5+ reformate.

In accordance with a third aspect of the present disclosure, there is provided a system for separating and purifying aromatic hydrocarbons, which comprises:
a feed line of an aromatic hydrocarbon-containing feedstock having a bromine index of at least 30;
a hydrogen feed line;
a hydrogenation reactor communicating with each of the feed line of the feedstock and the hydrogen feed line, the hydrogenation reactor filled with a multi-stage catalyst bed, in which the multi-stage catalyst bed comprises a first catalyst bed comprising at least one stage and at least one second catalyst bed disposed at the downstream of the first catalyst bed, along a flow direction of the feedstock transferred through the feed line; and
at least one separator communicating with the hydrogenation reactor, the separator separating a product containing at least one aromatic hydrocarbon selected from the group consisting of C6 aromatics, C7 aromatics, C8 aromatics and C9+ aromatics, among products discharged from the hydrogenation reactor,
wherein,
the first catalyst bed comprises a support containing inorganic oxide, and at least one active metal selected from the group consisting of Ni, Pd, Pt, Ru, Re, Co, Mo, Co—Mo, Ni—Mo, and Ni—W, in which, among the active metals, each of Re, Co, Mo, and Co—Mo is a reduced or sulfide form, and each of Ni, Pd, Pt, Ru, Ni—Mo and Ni—W is a sulfide form, and
the second catalyst bed comprises a support containing inorganic oxide, and Ni—Mo and/or Ni—W in a reduced form as an active metal.

In accordance with a fourth aspect of the present disclosure, there is provided a system for separating and purifying aromatic hydrocarbons, which comprises:
a feed line of an aromatic hydrocarbon-containing feedstock having a bromine index of at least 30;
a hydrogen feed line;
a multi-stage hydrogenation unit communicating with each of the feed line of the feedstock and the hydrogen feed line, in which the multi-stage hydrogenation unit comprises a first reaction unit containing at least one first catalyst and a second reaction unit communicating with the first reaction unit at the downstream of the first reaction unit and containing a second catalyst, along a flow direction of the feedstock transferred through the feed line; and
at least one separator communicating with the multi-stage hydrogenation unit, the separator separating a product containing at least one aromatic hydrocarbon selected from the group consisting of C6 aromatics, C7 aromatics, C8 aromatics, and C9+ aromatics, among products discharged from the multi-stage hydrogenation unit,
wherein,
the first catalyst comprises a support containing inorganic oxide, and at least one active metal selected from the group consisting of Ni, Pd, Pt, Ru, Re, Co, Mo, Co—Mo, Ni—Mo, and Ni—W, in which, among the active metals, each of Re, Co, Mo, and Co—Mo is a reduced or sulfide form, and each of Ni, Pd, Pt, Ru, Ni—Mo and Ni—W is a sulfide form, and
the second catalyst comprises a support containing inorganic oxide, and Ni—Mo and/or Ni—W in a reduced form as an active metal.

According to an exemplary embodiment, the system for separating and purifying aromatic hydrocarbons may further comprise a transalkylation unit for converting a fraction containing C6 aromatics, C7 aromatics and/or C9+ aromatics, among the aromatic hydrocarbon-containing product separated from the at least one separator, into C8 aromatics.

According to an exemplary embodiment, the system for separating and purifying aromatic hydrocarbons may further comprise a recycling line for recycling unrecovered C8 aromatics after separating and recovering para-xylene from the C8 aromatic hydrocarbon-containing product.

According to an exemplary embodiment, the system for separating and purifying aromatic hydrocarbons may further comprise:
a para-xylene separation/recovery unit for separating/recovering para-xylene from the C8 aromatics among the aromatic hydrocarbon-containing product separated from the at least one separator, and
a xylene isomerization unit for isomerizing unseparated/unrecovered C8 aromatics, other than the para-xylene to form an increased content of para-xylene.

According to an exemplary embodiment, the system for separating and purifying aromatic hydrocarbon may further comprises a recycling line for recycling the remaining xylene fraction after separating/recovering para-xylene among the aromatic fraction discharged from the xylene isomerization unit.

BRIEF DESCRIPTION OF THE DRAWINGS

The above and other objects, features and other advantages of the present disclosure will be more clearly understood from the following detailed description taken in conjunction with the accompanying drawings, in which.

DESCRIPTION OF THE INVENTION

Figure 1:
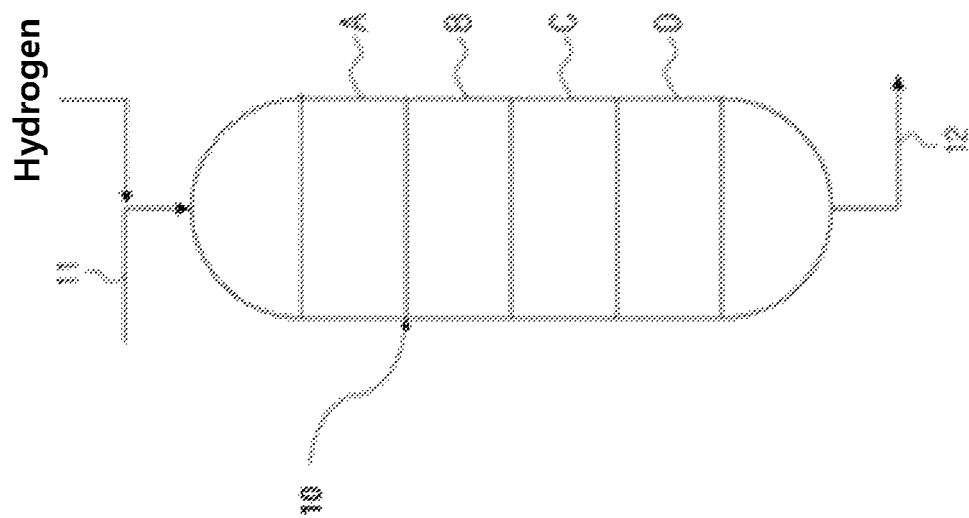
FIG. 1 is a schematic diagram illustrating a catalyst system based on a reactor filled with a plurality of catalyst beds for selectively hydrogenating and removing unsaturated hydrocarbons in an aromatic fraction according to an exemplary embodiment.

The present disclosure can be worked in its entirety with reference to the following description. It is to be understood that the following description illustrates preferable embodiments of the present disclosure, but the present disclosure is not necessarily limited thereto. It is also to be understood that the accompanying drawings are included to provide a further understanding of the present disclosure, and are not intended to limit the scope of the present disclosure.

The terms used herein are defined as follows.

As used herein, the term "heterogeneous catalyst" refers to a catalyst that is present in a different phase from a reactant in a catalytic reaction. For example, a heterogeneous catalyst may remain undissolved in a reaction medium. When a heterogeneous catalyst is used, the reaction begins with the diffusion and adsorption of reactants onto the surface of the heterogeneous catalyst. After completion of the reaction, the product needs to be desorbed from the surface of the heterogeneous catalyst.

As used herein, the term "support" refers to a material (typically a solid-phase material) having a large specific surface area, onto which a catalytically active component is attached or deposited, and the support may or may not be involved in a catalytic reaction.

As used herein, the term "olefins" may be intended to include alkenes, cycloalkenes, alkenyl benzenes and the like.

As used herein, the term "disproportionation" refers to the transfer of alkyl radical from one molecule to the other in order to form two different products between same kind of molecules. For example, disproportionation of toluene may result in the production of benzene and xylene.

In a narrow sense, the term "transalkylation" refers to a reaction in which at least one alkyl radical (e.g., methyl, ethyl, propyl, butyl, or the like) is transferred from an organic compound to another.

As used herein, the term "dealkylation" refers to a reaction in which at least one alkyl group (e.g., methyl, ethyl, propyl, butyl, or the like) is eliminated from a hydrocarbon compound (specifically, an aromatic compound).

As used herein, the term "xylene isomerization" refers to isomerization of converting C8 aromatic hydrocarbons, more specifically ortho-xylene and/or meta-xylene, to para-xylene.

As used herein, the term "Cn+ aromatic" refers to an aromatic hydrocarbon having Cn or more carbon atoms, and similarly, the term "Cn-aromatic" refers to an aromatic hydrocarbon having Cn or fewer carbon atoms.

As used herein, the term "Cn+ hydrocarbon" refers to a hydrocarbon having Cn or more carbon atoms, and similarly, the term "Cn-hydrocarbon" refers to a hydrocarbon having Cn or fewer carbon atoms.

As used herein, the term "C8 aromatics" refers to aromatic hydrocarbons including mixed xylene (ortho-xylene, meta-xylene and para-xylene) and/or ethylbenzene.

As used herein, the term "bromine index (BI)" refers to a measured value (mg) of bromine consumed by 100 g of a hydrocarbon or hydrocarbon mixture, and may be used to indicate the percentage of unsaturated bonds present in the hydrocarbon. The bromine index may be measured, for example, according to ASTM D 2710-92.

As used herein, the term "rich" means that a particular compound is present, for example, in an amount of at least about 50%, specifically at least 70%, more specifically at least about 80%, particularly specifically, at least about 90%, on a predetermined basis (e.g., on a weight, volume or molar basis), in a fraction or a stream.

As used herein, the term "separator" may be construed to broadly include any unit, apparatus, column, stabilizer, extractor, or the like, which involve physical separation.

Unless otherwise stated, an aromatic ring itself is excluded from the scope of the unsaturated hydrocarbons, which are to be removed by selective hydrogenation, even though it contains double bonds therein.

Olefin Selective Hydrogenation Catalyst System

According to one embodiment of the present disclosure, in order to remove unsaturated hydrocarbon compounds (specifically, olefins, acetylenes, and/or styrene (or its derivatives)) present in trace amounts in an aromatic fraction (e.g., an alkyl aromatic fraction) through selective hydrogenation, a plurality of hydrogenation catalysts having different catalytic activities are disposed within a single reactor in a staged loading manner, or a plurality of reactors are arranged in such a way as to be equivalent with the staged loading.

In this regard, the catalysts are loaded stepwise in the hydrogenation reactor such that at least one first catalyst (or first catalyst bed) and the second catalyst (or second catalyst bed) are sequentially disposed along the flow direction of the feedstock. At this time, notably, the first catalyst bed is composed of a catalyst that results in relatively low aromatic loss in spite of having relatively low durability during the selective hydrogenation of unsaturated hydrocarbons in the aromatic fraction, while the second catalyst is composed of a catalyst that brings about relatively high aromatic loss during the hydrogenation, but has excellent durability, thereby improving the selective removal rate of unsaturated hydrocarbons and durability while suppressing aromatic loss in the overall reaction system.

In an exemplary embodiment, the plurality of hydrogenation catalysts may largely include the first catalyst and the second catalyst, and the first catalyst and the second catalyst are charged or filled by stacking in the form of a bed (i.e., the first catalyst bed and the second catalyst bed) into a single reactor for staged loading. At this time, the aromatic hydrocarbon-containing feedstock introduced into the hydrogenation reactor is subjected to hydrogenation while contacting the first catalyst (or catalyst bed) and the second catalyst (or catalyst bed) together with hydrogen in that order.

In addition, the first catalyst bed may be composed of a single catalyst, but may be provided in the form of a catalyst bed in which two or more types of catalysts different from each other are staged or stacked. At this time, in the hydrogenation region, the feedstock first comes into contact with the first catalyst. As the hydrogen supplied into the hydrogenation reactor is first consumed through the hydrogenation by the first catalyst (or catalyst bed), the less amount of hydrogen is contacted with the second catalyst (or catalyst bed) located downstream, compared to the first catalyst.

As described above, because a relatively high partial pressure of hydrogen is applied to the first catalyst, when the saturation of aromatics (particularly, benzene ring) as well as unsaturated hydrocarbons is strong during the hydrogenation, the total aromatic yield is decreased. On the other hand, in the region where the second catalyst is located, a considerable amount of hydrogen has already been consumed through the hydrogenation by the first catalyst at the upstream, thereby creating an atmosphere in which aromatic loss due to hydrogenation is suppressed. Therefore, a catalyst having good durability despite high aromatic loss can be disposed as the second catalyst.

First Catalyst

In consideration of the above, in this embodiment, the first catalyst is composed of materials capable of minimizing aromatic loss in spite of somewhat low catalyst durability (that is, the property capable of maintaining hydrogenation activity even upon long-term operation), and the second catalyst is composed of materials having excellent durability in spite of somewhat strong aromatic saturation characteristics. In addition, in a specific embodiment, the first catalyst may be composed of materials exhibiting high hydrogenation activity to an unsaturated hydrocarbon (i.e., the materials having a high BI reduction ability) in addition to the above-described characteristics.

According to one embodiment, the first catalyst is a supported catalyst which comprises a support containing inorganic oxide, and at least one active metal selected from the group consisting of Ni, Pd, Pt, Ru, Re, Co, Mo, Co—Mo, Ni—Mo and Ni—W.

In an exemplary embodiment, the content of the active metal in the first catalyst is, for example, about 0.5 to 40% by weight, specifically about 2 to 30% by weight, and more specifically about 4 to 25% based on the total weight of the catalyst. These metal content ranges are provided only for illustrative purposes, and may vary with the type of active metal that is used, the hydrogenation activity thereof, the form of the metal, and the like.

An embodiment of the first catalyst using a plurality of metals among the active metals exemplified above may be combined as below:

In the case of Co—Mo, the atomic ratio of cobalt to molybdenum may be adjusted within a range of, for example, 1:about 0.5 to 10, specifically 1:about 1 to 5, and more specifically 1:about 1.5 to 3. Further, in the case of Ni—Mo, the atomic ratio of nickel to molybdenum may be adjusted within a range of, for example, 1:about 0.5 to 10, specifically 1:about 1 to 5, and more specifically 1:about 1.5 to 3. In addition, in the case of Ni—W, the atomic ratio of nickel to tungsten may be adjusted within a range of, for example, 1:about 0.5 to 10, specifically 1:about 1 to 5, and more specifically 1:about 1.5 to 3.

In one embodiment, when the active metal in the first catalyst is Re, Co, Mo, and/or Co—Mo, it may be a reduced form or a sulfide form. When Ni, Pd, Pt, Ru, Re, Co, Mo, and Co—Mo as active metals are sulfide forms, they exhibit an excellent effect of suppressing aromatic loss, but relatively low ability to remove unsaturated hydrocarbons (e.g., olefins, and/or styrene). In a specific embodiment, when the active metal in the first catalyst is Re, Co, Mo, or Co—Mo, it may be a reduced form and thus may have higher hydrogenation activity than the sulfide form but lower durability than the second catalyst.

In addition, when the active metal in the first catalyst is Ni, Pd, Pt, Ru, Ni—Mo and/or Ni—W, it may be a sulfide form because the reduced form exhibits excellent hydrogenation and removal efficiency of unsaturated hydrocarbons but increased aromatic loss.

According to an exemplary embodiment, the inorganic oxide constituting the support may be selected from materials having a large specific surface area, and may, for example, include at least one selected from the group consisting of alumina, silica, silica-alumina, aluminum phosphate, zirconia, titania, bentonite, kaolin, clinoptilolite, and montmorillonite.

According to a specific embodiment, the inorganic binder may be amorphous, and in particular, may be at least one selected from the group consisting of alumina, silica and silica-alumina, in particular, alumina and/or silica.

According to an exemplary embodiment, the support may be in a cylindrical shape, and may, for example, have a diameter of about 0.5 to 5 mm (specifically about 1 to 3 mm), and a length of about 3 to 20 mm (specifically about 5 to 15 mm). Alternatively, the support may have a shape such as granule, pellet, tablet or sphere, in addition to the cylindrical shape. As described above, in order to manufacture a support having a specific shape, a molding method known in the art, such as extrusion, spray drying, pelletizing or oil dropping, may be applied, but this is provided for exemplary purpose.

According to an exemplary embodiment, the support may have an apparent density within the range of about 0.3 to 1.2 g/cc, specifically about 0.4 to 1.1 g/cc, and more specifically about 0.4 to 0.9 g/cc. In addition, the support may have an average pore diameter, for example, within the range of about 3 to 1,000 nm, specifically about 5 to 800 nm, and more specifically about 7 to 600 nm. In addition, the support may have a specific surface area (BET), for example, within the range of about 10 to 1,000 m$^2$/g, specifically about 30 to 800 m$^2$/g, and more specifically about 50 to 600 m$^2$/g. The numerical ranges of the above-described physical properties may be provided for exemplary purposes.

In an exemplary embodiment, with regard to the first catalyst, the active metal may be loaded onto the support by known techniques in the art, for example, the impregnation (e.g., incipient wetness impregnation, excess solution impregnation and immersion), ion exchange, coprecipitation or the like.

Typically, the impregnation can be applied, for example, by adding a soluble metal precursor or compound (typically a water-soluble or solvent-soluble metal compound), particularly a metal salt, to a liquid medium selected from water, an acid aqueous solution, a basic aqueous solution, etc., and filling the pores of the support with the resulting mixture.

In an exemplary embodiment, the applicable metal precursor may generally be a salt, complex, or halide of an active metal, and may be illustrated as follows.

For example, molybdenum precursors may include at least one selected from the group consisting of molybdenum (II) acetate, ammonium (VI) molybdate, diammonium (III) dimolybdate, ammonium (VI) heptamolybdate, ammonium (VI) phosphomolybdate and similar sodium and potassium salts, molybdenum (III) bromide, molybdenum(III)-(V) chloride, molybdenum (VI) fluoride, molybdenum (VI) oxychloride, molybdenum(IV)-(VI) sulfide, molybdic acid and ammonium, sodium and potassium salts thereof, and molybdenum (II-VI) oxide, but is not necessarily limited thereto.

The cobalt precursor may include at least one selected from the group consisting of nitrate, sulfate, carbonate, acetate, alkoxide, and halide of cobalt. Specifically, the cobalt precursor, for example, may include at least one selected from cobalt nitrate, cobalt sulfate, cobalt acetate, cobalt carbonate, cobalt hydroxide, cobalt alkoxide, cobalt halide (e.g., cobalt chloride, cobalt bromide, etc.), hydrates thereof and the like. More specifically, the cobalt precursor may be cobalt nitrate and/or a hydrate thereof (e.g., Co(NO$_3$)$_2$·6H$_2$O).

The nickel precursor may, for example, include at least one selected from nickel nitrate, nickel sulfate, nickel phosphate, nickel halide, nickel carboxylate, nickel hydroxide, nickel carbonate, an acetylacetonate nickel complex, nickel acetate, and hydrates thereof. More specifically, the nickel precursor may be nickel nitrate and/or a hydrate thereof (e.g., Ni(NO$_3$)$_2$·6H$_2$O).

The tungsten precursor may, for example, include at least one selected from ammonium metatungstate, ammonium tungstate, sodium tungstate, tungstic acid, tungsten chloride, and the like.

The palladium precursor may include at least one selected from palladium acetate, palladium chloride, palladium nitrate, palladium sulfate, and the like.

The platinum precursor may include at least one selected from chloroplatinic acid, ammonium chloroplatinate, dinitrodiaminoplatinum, tetrachromodiaminoplatinum, hexachromodiaminoplatinum, dichlorodiaminoplatinum, platinum dichloride (II), platinum tetrachloride (IV) and the like.

The ruthenium precursor may include at least one selected from ruthenium chloride, ruthenium nitrosyl nitrate, chlorohexaamino ruthenium, and the like.

The rhenium precursor may include at least one selected from perrhenic acid, rhenium chloride, ammonium perrhenate, potassium perrhenate, rhenium oxide and the like.

According to an exemplary embodiment, the concentration of the active metal in the impregnation solution may range from, for example, about 0.005 to 5 M, specifically about 0.01 to 3 M, and more specifically about 0.015 to 2 M. The conditions of the impregnation are not particularly limited, and, for example, the impregnation process may be performed at about 1 to 100° C. (specifically about 25 to 60° C.) for about 0.1 to 48 hours (about 0.5 to 12 hours), but these conditions are provided for exemplary purposes.

As described above, the active metal may be impregnated onto the support and then subjected to a drying process. For example, the drying may be performed in an oxygen-containing atmosphere (specifically, air), at a temperature of, for example, in the range of about 60 to 200° C., specifically in the range of about 80 to 150° C. In addition, the drying time may be determined within a range of, for example, about 0.5 to 15 hours, specifically about 1 to 12 hours. The metal precursor may be more tightly attached onto the support through the drying process.

Then, the dried catalyst is calcined (or heat-treated), and the calcination is performed in an oxygen-containing atmosphere (e.g., air) or an inert gas (e.g., nitrogen, etc.) atmosphere, more particularly an oxygen-containing atmosphere. Further, the calcination temperature may be determined within the range of, for example, about 300 to 800° C., specifically about 400 to 650° C. In addition, the calcination time may be adjusted within the range of, for example, about 0.5 to 24 hours, specifically about 1 to hours. When the calcination is performed in an oxygen-containing atmosphere, the active metal may be converted to an oxide form; for example, molybdenum may be converted to MoO$_3$ and nickel may be converted to NiO.

Reduction Treatment

According to one embodiment, as described above, when the first catalyst includes, as the active metal, Re, Co, Mo, and/or Co—Mo, a reduction treatment is performed on the calcined first catalyst for conversion into a fully/partially reduced form.

In this regard, the reduction treatment may be performed using hydrogen alone or hydrogen diluted in an inert gas (e.g., N$_2$, He, Ar, etc.) at a temperature of, for example, about 25 to 800° C., specifically about 200 to 700° C., and more specifically about 300 to 550° C., and the reduction treatment time is not particularly limited, and may be, for example, adjusted within the range of about 0.5 to about 24 hours, specifically about 1 to about 12 hours.

Through the above-described process, the active metal may be present in a reduced form in the first catalyst. Illustratively, the metal contained in the catalyst is present in an elemental form or partially oxidized form (for example, when the first metal is molybdenum (Mo), Mo$^{6+}$ is partially oxidized to Mo$^{4+}$) through reduction treatment.

Sulfidation (Sulfide Treatment)

In order to control excessive hydrogenation activity that induces side reactions such as loss of aromatics, or to impart a hydrogenation function depending on the supported metal (particularly in the case of molybdenum), the active metal may be converted to a sulfide form rather than a reduced form in an optional step.

According to an exemplary embodiment, the reduction-treated catalyst may be sulfided. As described above, when the active metal in the first catalyst is Ni, Pd, Pt, Ru, Re, Co, Mo, Co—Mo, Ni—Mo and Ni—W, it may be present in the form of a sulfide.

In this regard, metal components in the catalyst can be converted into sulfides by methods known in the art, and such sulfidation may be a gas-phase method (contacting hydrogen sulfide or a mixture of an inert gas with hydrogen sulfide) or a liquid-phase method (contacting sulfur compound-containing solution). According to a specific embodiment, the reduction-treated catalyst may be treated with a sulfur compound-containing solution.

According to an exemplary embodiment, the sulfur compound useful for the sulfidation may include at least one selected from hydrogen sulfide, hydrogen disulfide, carbon disulfide, alkyl sulfide, and the like. In particular, as the alkyl sulfide, for example, methyl sulfide, dimethyl sulfide, dimethyl disulfide, diethyl sulfide, and/or dibutyl sulfide may be used. In addition, hydrocarbon-based solvents such as benzene, toluene, xylene, C9+ aromatics, hexane, and heptane may be used as solvents for sulfidation. By way of example, the amount of the sulfur compound in the solution for sulfidation may be appropriately determined to be an amount greater than the equivalent amount required to convert the metal in the catalyst to sulfide. For example, when molybdenum is used as the active metal, a sulfur compound in equal or more amount required for converting molybdenum into, as a sulfide, $MoS_3$ (which can be finally converted to $MoS_2$) may be mixed with a solution. In addition, nickel may be converted to $Ni_3S_2$.

In an exemplary embodiment, the sulfidation may be performed at a temperature of, for example, room temperature to about 500° C. (specifically, about 100 to 450° C.) for about 0.5 to about 100 hours (specifically, for about 1 to 48 hours).

Second Catalyst

According to one embodiment, the aromatic-containing fraction that has undergone hydrogenation through the first catalyst is subjected to an additional hydrogenation process in the presence of the second catalyst. As described above, the additional hydrogenation process is designed such that hydrogen introduced into a single reactor is consumed as the hydrogenation by the first catalyst proceeds, and on the second catalyst (or catalyst bed) located downstream of the first catalyst, hydrogen (or hydrogen partial pressure) is supplied in an amount lower than in the case of the first catalyst.

In the above-described reaction environment, a catalyst having high hydrogenation activity and excellent durability in spite of causing aromatic loss may be used as the second catalyst. In this case, the effects of efficiently removing unsaturated hydrocarbons through selective hydrogenation, maintaining long-term activity and suppressing aromatic loss can be achieved at the same time. It is noteworthy that the synergistic improvements resulting from this design remarkably exceed the level expected from a simple combination of different first and second catalysts.

In order to achieve the above advantages, according to an embodiment, the second catalyst may be a catalyst supporting a reduced form of Ni—Mo and/or Ni—W as an active metal on a support containing inorganic oxide. More specifically, the second catalyst may be a catalyst supporting a reduced form of Ni—Mo.

In an exemplary embodiment, when the active metal in the second catalyst is Ni—Mo, the atomic ratio of nickel to molybdenum is, for example, adjusted within the range of about 1:about 0.5 to 10, specifically 1:about 1 to 5, more specifically 1:about 1.5 to 3. Moreover, in the case of Ni—W, the atomic ratio of nickel to tungsten may be adjusted within the range of, for example, 1:about 0.5 to 10, specifically 1:about 1 to 5, and more specifically 1:about 1.5 to 3.

In this regard, the support for the second catalyst may be at least one selected from the species as set forth previously in connection with the first catalyst. In addition, the support for the first catalyst and the support for the second catalyst may be the same or different.

The content of the active metal in the second catalyst may be determined in the range of, for example, about 2 to about 40% by weight, specifically about 3 to about 30% by weight, and more specifically about 4 to about 25% by weight, based on the total weight of the catalyst. These metal content ranges are provided for exemplary purposes.

In addition, the metal precursor used for the preparation of the second catalyst, the properties of the support, the supporting method, and the drying/calcination and reduction treatments may be the same as those described above in connection with the first catalyst, without particular limitation.

A catalyst system based on a reactor filled with a plurality of catalyst beds for removing unsaturated hydrocarbons in an aromatic fraction through selective hydrogenation according to an exemplary embodiment of the present disclosure is shown in FIG. 1.

Referring to FIG. 1, a plurality of hydrogenation catalysts is charged in a reactor 10 in the staged loading manner. In the embodiment shown, four types of catalyst beds (A, B, C and D) are charged or disposed along the introduction direction of a feedstock 11, wherein the catalyst beds (A, B and C) correspond to the first catalysts and the catalyst bed D located in the last stage corresponds to the second catalyst. This arrangement is provided for illustrative purposes. Thus, the first catalyst may be composed of multiple beds including a plurality of catalysts or a catalyst bed including a single catalyst.

According to an exemplary embodiment, the amount of the first catalyst loaded in the reactor 10 may be changed depending on the type of catalyst (active metal and/or support), but is, for example, adjusted within the range of about 10 to about 90%, specifically about 20 to about 80%, and more specifically about 30 to about 70%, based on the total volume of the first catalyst and the second catalyst.

As described above, the active metal in each of the first catalyst beds (A, B and C) includes at least one selected from the group consisting of Ni, Pd, Pt, Ru, Re, Co, Mo, Co—Mo, Ni—Mo, and Ni—W, among which each of Re, Co, Mo, and Co—Mo is a reduced form or a sulfide form and each of Ni, Pd, Pt, Ru, Ni—Mo, and Ni—W is a sulfide form. In addition, each of the three types of catalyst beds corresponding to the first catalyst may be the same as or different from one another. Meanwhile, in the case of the second catalyst bed D, the active metal includes a reduced form of Ni—Mo and/or Ni—W.

According to the illustrated embodiment, an aromatic-containing feedstock, specifically an aromatic-rich feedstock, is introduced through an upper inlet of the reactor 10, and hydrogen is also supplied onto the first catalyst to provide hydrogen necessary for the hydrogenation when the feedstock contacts the first catalyst. In this regard, FIG. 1 shows introducing hydrogen combined with the feedstock (or at least part of hydrogen dissolved in the feedstock) into the reactor 10 through the flow line of the feedstock 11. Alternatively, hydrogen may be introduced into the reactor 10 through a separate flow line.

The hydrogen thus supplied is consumed through the hydrogenation while sequentially passing through the first catalyst beds A, B and C together with the feedstock, and hydrogen is supplied to the second catalyst bed D in a lower amount than the amount of hydrogen supplied to the uppermost catalyst bed A among the first catalysts. As such, the hydrogenation product 12 that has passed through the first catalyst and the second catalyst is discharged to a subsequent process through the bottom of the reactor 10.

Figure 2:
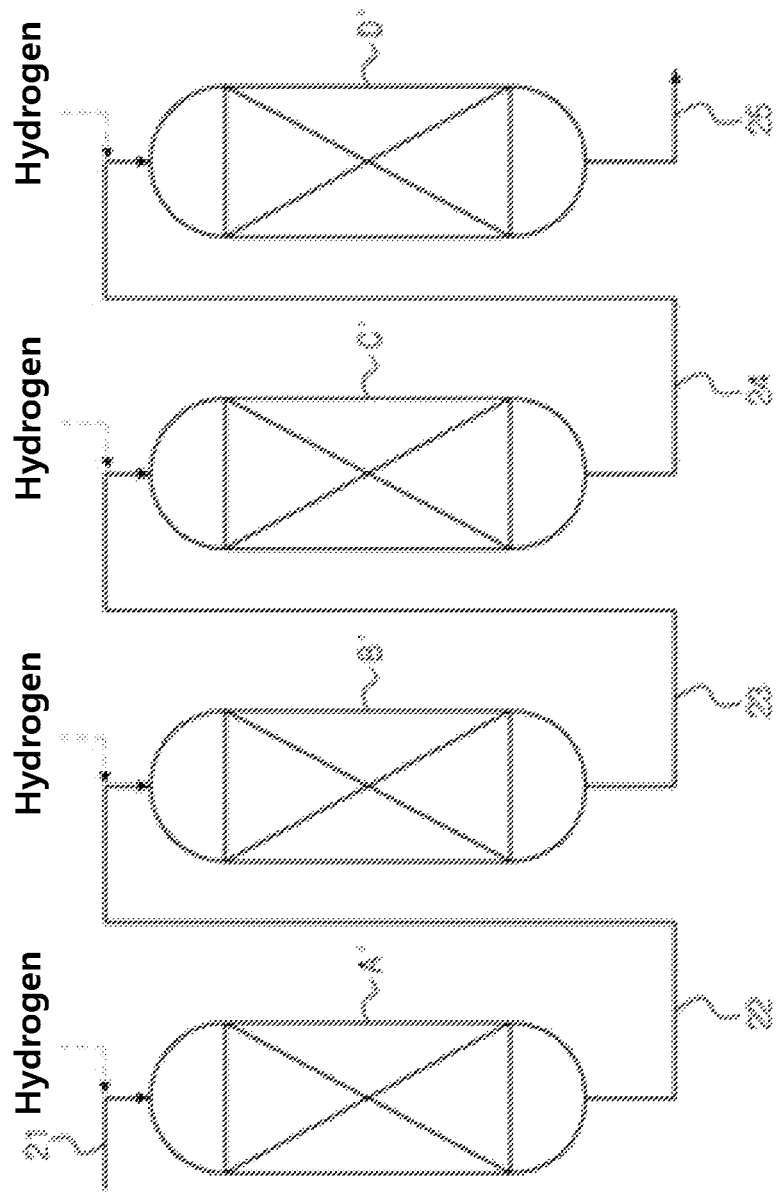
FIG. 2 is a schematic diagram illustrating a catalyst system for selectively hydrogenating and removing unsaturated hydrocarbons in an aromatic fraction using a plurality of reactors connected in series according to an exemplary embodiment, where hydrogen may be introduced only into the first reactor, or into each reactor.

Meanwhile, according to another exemplary embodiment of the present disclosure, a schematic catalyst system for selectively hydrogenating and removing unsaturated hydrocarbons in an aromatic fraction using a plurality of reactors connected in series is shown in FIG. 2.

The illustrated embodiment is substantially the same as the catalyst configuration shown in FIG. 1 except that a plurality of reactors are used. As an example, each of the first to third reactors (A', B' and C') is filled with a first catalyst to construct a first reaction unit, while the fourth reactor D' is filled with a second catalyst to construct a second reaction unit. The above-described reactor arrangement may be provided for exemplary purposes, and each of the first and second reactors may be filled with the first catalyst, and each of the third and fourth reactors may be filled with the second catalyst. In addition, a reactor arrangement may be designed such that two reactors are used, a reactor filled with a first catalyst is disposed at the upstream, and a reactor filled with a second catalyst is disposed (or connected) in series therewith at the downstream thereof.

Referring to FIG. 2, an aromatic-containing feedstock 21 is introduced into a first reactor A' in the first reaction unit, is subjected to hydrogenation by the first catalyst under supply of hydrogen, and is then introduced into a second reactor B' through a line 22. In addition, an intermediate hydrogenation product discharged from the second reactor B' is introduced into a third reactor C' through a line 23 and is discharged after additional hydrogenation. Then, the intermediate hydrogenation product, which has passed through the third reactor C', is introduced into a fourth reactor D' in the second reaction unit through a line 24, is subjected to hydrogenation by the second catalyst, and is discharged from the fourth reactor D' through a line 25.

Referring again to FIG. 2, hydrogen required for the hydrogenation is supplied to the first reactor A' and consumed during the hydrogenation, dissolved in the hydrocarbon fraction, and then discharged. In this case, the aromatic-containing fraction 24, which has been introduced from the second reactor B' to the fourth reactor D' via the third reactor C', contains hydrogen, and is subjected to the final hydrogenation under the condition in which a small amount of hydrogen is supplied compared to the upstream reactors thereof.

In this case, in the reactors connected to the downstream of the first reactor A', in particular, in the fourth reactor D', hydrogen may be supplied in a smaller amount than the level required for hydrogenation. Therefore, as shown in the drawing, any optional hydrogen feed line is installed not only in the first reactor but also in each of the second to fourth reactors, so that hydrogen can be further supplied, and the appropriate amount of hydrogen for hydrogenation can be supplied by controlling the amount of hydrogen in each hydrogen supply line through valve operation.

According to an alternative embodiment, a plurality of reactors filled with the catalyst described above may be disposed using a stacking method. In this case, any conduit connecting or communicating between the reactors may be omitted, or the length thereof may be reduced. In addition, by dividing the hydrogen feed line, hydrogen can be supplied between the stacked reactors, and thus an optimum hydrogen atmosphere can be formed.

According to an exemplary embodiment, the loading ratio of the first catalyst and the second catalyst used in each of the reactors A' to C' filled with the first catalyst and the reactor D' filled with the second catalyst may be adjusted within the range of, for example, about 10 to 90%, specifically about 20 to 80%, and more specifically about 30 to 70%, based on the total volume of the first catalyst and the second catalyst, similar to the above.

Process and System for Purifying Aromatic-Containing Hydrocarbon Fraction

According to another embodiment of the present disclosure, the purification of an aromatic-containing hydrocarbon fraction is performed by selectively hydrogenating an unsaturated hydrocarbon present in the aromatic-containing hydrocarbon fraction, specifically an aromatic-rich hydrocarbon fraction, using the above-described multiple catalyst bed system or a multi-stage catalyst system based on a plurality of reactors.

In this regard, the boiling point of the aromatic-containing hydrocarbon fraction (i.e., feedstock) may range from, for example, about 35 to 300° C., specifically about 40 to 250° C., and more specifically about 50 to 220° C. According to an exemplary embodiment, the aromatic-containing hydrocarbon fraction may contain an alkyl aromatic hydrocarbon. For example, the alkyl aromatic hydrocarbon may be, for example, an about C6 to about C18 alkyl aromatic hydrocarbon, specifically an about C6 to about C16 alkyl aromatic hydrocarbon.

In this regard, the alkyl aromatics contain an aromatic ring having at least one alkyl radical attached thereto. Examples of the alkyl radical include methyl, ethyl, propyl, and butyl. The alkyl aromatics may be exemplified by toluene, ethyl toluene, propyl benzene, tetramethyl benzene, ethyldimethyl benzene, diethyl benzene, methylpropyl benzene, ethylpropyl benzene, triethyl benzene, diisopropylbenzene, and a mixture thereof.

In addition, the feedstock may further contain aromatics having no alkyl substituents thereon, such as benzene as well as the above-described alkyl aromatics. In an exemplary embodiment, the feedstock may contain benzene, toluene, xylene, and/or C9+ aromatics.

However, it should be noted that, in this embodiment, the aromatic-containing feedstock may contain unsaturated hydrocarbons that increase a bromine index (BI), such as hydrocarbons having at least one double bond and/or triple bond, e.g., mono-olefins, di-olefins, acetylenes and styrene (or its derivatives). Such unsaturated hydrocarbons are the target for selective hydrogenation. In addition, the content of unsaturated hydrocarbons in the aromatic-containing feedstock can be quantified by the bromine index. In this embodiment, the bromine index of the feedstock is, for example, within the range of at least about 30, specifically 40 to 15,000, more specifically about 50 to about 10,000, in particular, about 100 to about 8,000.

According to an exemplary embodiment, the aromatic-containing feedstock is an aromatic-rich feedstock, and the aromatic content ranges from, for example, at least about 50% by weight, specifically at least about 70% by weight, and more specifically about 80% by weight or more. In addition, the aromatic-containing feedstock may contain saturated hydrocarbons, wherein the saturated hydrocarbons may be present in an amount of, for example, about 50% by weight or less, specifically about 30% by weight or less, and more specifically about 20% by weight or less.

According to an exemplary embodiment, the aromatic-containing feedstock may be derived from: catalytic reformation of naphtha; thermal cracking of naphtha, distillates, or other hydrocarbons capable of producing light olefins and aromatic-rich fractions; and catalytic or thermal cracking of heavy oil fractions capable of producing gasoline boiling range hydrocarbons. Such sources may be used alone or in combination as a feedstock.

According to an exemplary embodiment, the hydrogenation for removing unsaturated hydrocarbons in the aromatic-containing fraction is performed at a temperature selected within the range of, for example, room temperature to 300° C., specifically about 40 to 250° C., and more specifically about 50 to 230° C.

In addition, the hydrogenation system enables a liquid-phase reaction or a three-phase reaction (trickle bed) using an excessive amount of hydrogen. However, the liquid-phase reaction, which can reduce investment costs and may not require additional hydrogen separation due to the low residual amount of hydrogen after the reaction, may be more advantageous. The amount of hydrogen supplied thereto may be, for example, within the range of at least about 0.5 mol, specifically about 0.7 mol to about 20 mol, and more specifically about 1 to 10 mol with respect to 1 mol of unsaturated hydrocarbons contained in the feedstock. In the case where the amount of the hydrogen supply is excessively small or large, the removal rate of unsaturated hydrocarbons is low, or hydrogenation of the aromatic ring occurs, thus increasing the loss of aromatic hydrocarbons. However, the amount of hydrogen supply may be changed according to the properties of the feedstock, and thus is not limited to the range described above.

Meanwhile, according to exemplary embodiments, the pressure in the hydrogenation region may be selected within the range of, for example, about 3 to about 70 bar, specifically about 5 to about 30 bar, and more specifically about 7 to about 20 bar. When the pressure in the hydrogenation region is excessively low or high, the removal rate of unsaturated hydrocarbons is low, or hydrogenation of aromatic ring occurs, thus causing a problem of increased loss of aromatic hydrocarbons. Therefore, it is advantageous for the pressure in the hydrogenation region to be suitably controlled within the above-described range.

In addition, the space velocity (LHSV) of the aromatic-containing feedstock is controlled within the range of, for example, about 0.3 to about 30 $hr^{-1}$, specifically about 0.5 to about 20 $hr^{-1}$, and more specifically about 0.5 to about 10 $hr^{-1}$.

As described above, the feedstock containing unsaturated hydrocarbons in the aromatic fraction is sequentially brought in contact with the first catalyst (or catalyst bed) and the second catalyst (or catalyst bed) in the selective hydrogenation region to selectively remove only unsaturated hydrocarbons, and then is transferred to downstream processes, specifically, benzene, toluene or xylene product separation, or transalkylation, xylene isomerization, or the like, thereby yielding benzene, toluene, and xylene as target compounds. In this regard, the hydrogenation product has a reduced content of unsaturated hydrocarbons compared to the feedstock, and at least about 30% by weight, specifically at least about 70% by weight, more specifically at least about 80% by weight, even more specifically at least about 90% by weight, particularly specifically at least about 95% by weight of the unsaturated hydrocarbon in the feedstock may be removed by hydrogenation. According to particular embodiments, at least about 97%, specifically at least about 99%, and more specifically substantially all of the unsaturated hydrocarbons in the feedstock may be removed.

In addition, in this embodiment, the loss of aromatic hydrocarbons can be effectively suppressed while increasing the removal rate of unsaturated hydrocarbons by disposing two types of catalysts (i.e., the first catalyst and the second catalyst) in a particular manner in the catalyst system. In particular, as a result of disposing a reduced form of Ni—Mo and/or Ni—W supported catalyst as the second catalyst, durability can be enhanced so as to stably maintain catalytic activity even after long-term operation.

At this time, the aromatic loss in the aromatic hydrocarbon-containing product relative to the aromatic hydrocarbon-containing feedstock may be, for example, less than about 1% by weight, specifically less than about 0.3% by weight, and more specifically less than about 0.05% by weight.

Figure 3:
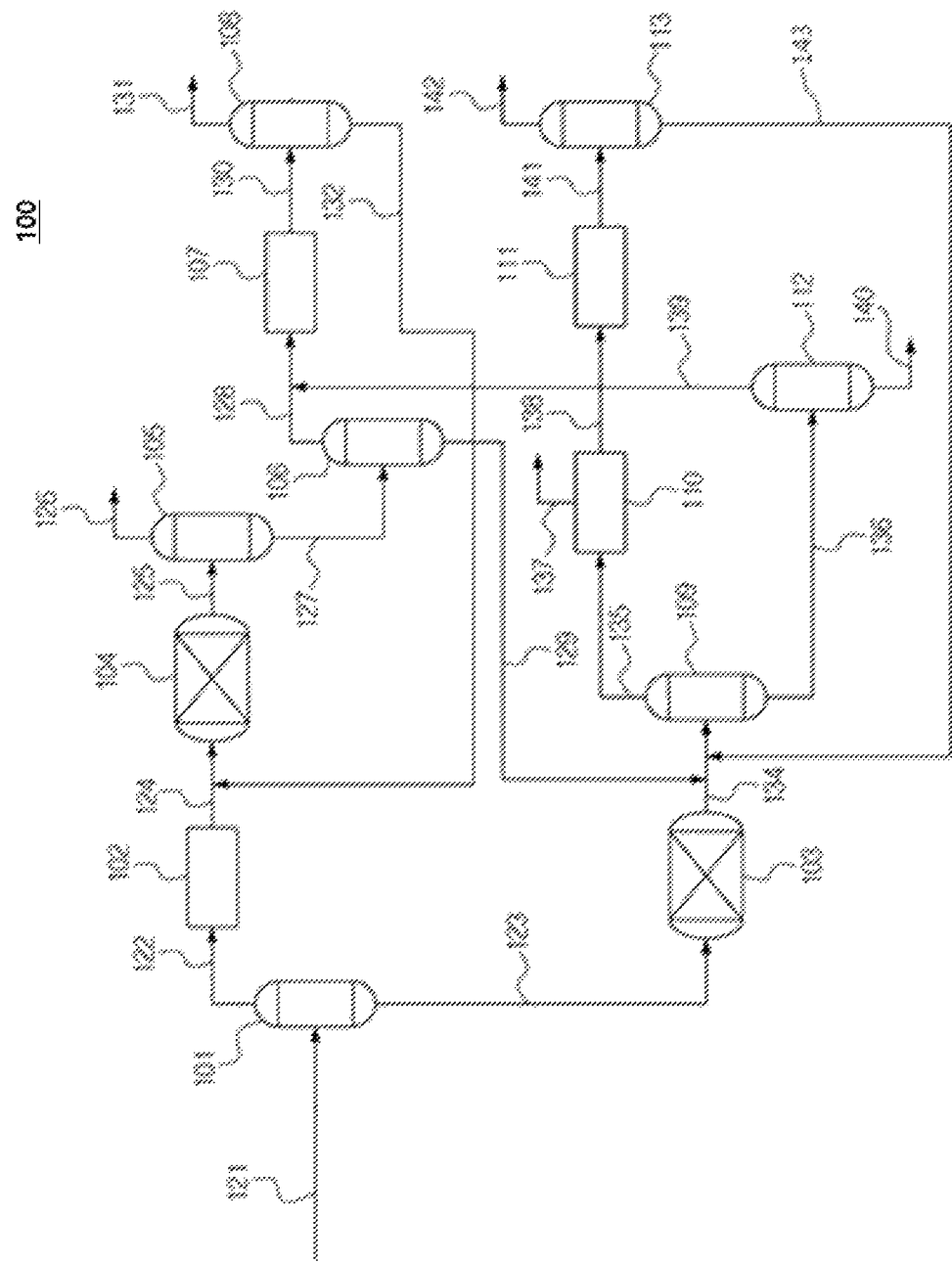
FIG. 3 is a schematic diagram illustrating a process for producing xylenes using selective hydrogenation of unsaturated hydrocarbons in an aromatic-containing feedstock according to an exemplary embodiment.

A xylene preparation process 100 using a step of selective hydrogenation of unsaturated hydrocarbons in the aromatic-containing feedstock according to an exemplary embodiment of the present disclosure is schematically shown in FIG. 3.

According to the illustrated embodiment, first, a C5+ reformate is used as an aromatic-containing feedstock 121, and is introduced into a splitter 101. In the splitter 101, the aromatic-containing feedstock 121 is split into a C7− hydrocarbon (specifically a C7− aromatic)-containing fraction 122 as an overhead stream, and a C8+ hydrocarbon (specifically a C8+ aromatic)-containing fraction 123 as a bottom stream.

At this time, the fraction 122 is transferred to a benzene/toluene extraction unit 102 to obtain a C6 and/or C7 aromatic-containing extract stream 124. As such, non-aromatic hydrocarbons, for example, paraffins and naphthenes may be separated as raffinates (not shown).

The extract stream 124 may contain small amounts of C8+ hydrocarbons (or aromatics) as well as C6 and/or C7 aromatics, and may also contain impurities that have not been completely removed during the extraction process. Moreover, the extract stream 124 may further contain components other than C6 and C7 aromatics because it is combined with a fraction 132 recycled from a first stabilizer 108, as will be described later. In particular, the extract stream 124 may contain unsaturated hydrocarbons to be removed in this embodiment as an impurity in the aromatic fraction 124.

Referring to FIG. 3, the C6 and/or C7 aromatic-containing fraction and the recycled fraction 132 are introduced into a first hydrogenation region 104 including a catalyst system configured in the staged loading manner described above or in a manner equivalent thereto, and the unsaturated hydrocarbons contained therein are selectively removed. As such, the C6/C7 aromatic-containing fraction 125 from which unsaturated hydrocarbons have been reduced or removed is transferred to a benzene column 105, where a C6 aromatic-containing fraction 126 is discharged as an overhead stream, and a C7 aromatic-containing fraction 127 is discharged as a bottom stream. At this time, as the C6 aromatic-containing fraction 126 split as the overhead stream may be a benzene-rich fraction, benzene may be recovered therefrom, and benzene with high purity may be recovered through an additional purification means or steps, if necessary.

Meanwhile, the C7 aromatic-containing fraction 127 discharged as the bottom stream of the benzene column 105 is transferred to a toluene column 106, where it is split into a C7 aromatic-rich fraction 128 as the overhead stream and a C8+ aromatic-rich fraction 129 as the bottom stream. At this time, the bottom stream 129 of the toluene column 106 contains C8 aromatics (i.e., xylenes) and thus may be selectively transferred to a xylene recovery process, as will be described later. The overhead stream 128 of the toluene column 106 is introduced into a transalkylation reaction unit 107, optionally together with a C9 aromatic-containing stream 139, as will be described below.

The transalkylation unit 107 may involve conversion of the C7 aromatic-rich fraction 128, or a stream containing the C9 aromatic-containing stream 139 combined therewith, into C8 aromatic hydrocarbons. Specifically, in the transalkylation unit 107, at least one of disproportionation, transalkylation, and dealkylation, for example, disproportionation of toluene, transalkylation of toluene/C9 aromatic compounds, dealkylation of alkyl aromatics, and the like may be performed, and C8 aromatics (specifically, mixed xylenes) may be produced through the above-described reaction. The reaction in the transalkylation unit 107 may be performed using known reaction conditions and catalysts, and thus detailed descriptions thereof will be omitted.

The C8 aromatic-containing product stream 130 resulting and discharged from the transalkylation is introduced into the first stabilizer 108 and is split into light hydrocarbons in the transalkylation product, for example, a C5− hydrocarbon-containing fraction 131 and a C6+ hydrocarbon (aromatic)-containing fraction 132. At this time, the fraction 132 may be recycled as described above, combined with the extract stream 124 discharged from the benzene/toluene extraction unit 102, and introduced into the first hydrogenation region 104.

Referring again to FIG. 3, the C8+ aromatic-containing stream 123, which is the bottom stream of the splitter 101, may contain unsaturated hydrocarbons, and thus may be introduced into a second hydrogenation unit 103, where the unsaturated hydrocarbons are selectively removed through hydrogenation. In this case, the second hydrogenation unit 103 may include the catalyst system configured in the staged loading manner described above or a manner equivalent thereto. In this regard, both the first hydrogenation unit 104 and the second hydrogenation unit 103 may equally use the catalyst system implemented in a staged loading manner. Alternatively, one of the first hydrogenation unit 104 and the second hydrogenation unit 103 may use the stage-loading typed catalyst system, while the other may use a conventional hydrogenation catalyst system. In another exemplary embodiment, one of the first hydrogenation unit 104 and the second hydrogenation unit 103 may be replaced with a conventional clay treatment unit, and the other may employ the stage-loading typed catalyst system. In yet another embodiment, the clay treatment unit may be added to upstream or downstream of at least one of the first hydrogenation unit 104 and the second hydrogenation unit 103.

The C8+ hydrocarbon-containing fraction 134, in which unsaturated hydrocarbons have been reduced by the second hydrogenation unit 103, may be combined with the bottom stream 129 of the toluene column 106 and/or the fraction 143 recycled from the splitter 113 as described below, and may then be transferred to the xylene column 109. In the xylene column 109, the fraction 134 may be split into a xylene-rich fraction 135 as an overhead stream and a C9+ aromatic-containing stream 136 as a bottom stream. The split xylene-rich fraction 135 is transferred to a para-xylene recovery unit 110, where para-xylene among C8 aromatics (i.e., mixed xylenes) is selectively split into a para-xylene-rich stream 137, and para-xylene is recovered therefrom. In this regard, an additional separation and/or purification means may be further provided in order to obtain high-purity para-xylene. Representative examples of such para-xylene recovery technology include Parex from UOP, Eluxyl from IFP, Aromax from Toray and the like.

The C8 aromatic-rich fraction 138 remaining after the para-xylene is separated from the xylene recovery unit 110 may contain mostly ortho-xylene and/or meta-xylene. The fraction 138 may be transferred to a xylene isomerization unit 111. In this regard, the stream 138 contains mixed xylenes in a non-equilibrium state (a xylene mixture in which at least one isomer of C8 aromatic compounds is present in a concentration different from the equilibrium concentration, for example, in which the concentration of para-xylene is lower than in the equilibrium state), and thus the xylene isomerization unit 111 performs isomerization to convert the xylenes in the non-equilibrium state to xylenes in the equilibrium state. The reaction in the xylene isomerization unit 111 may be performed using known reaction conditions and catalysts, and thus detailed descriptions thereof will be omitted.

The product 141 discharged through the xylene isomerization as described above is transferred to the splitter 113 and split into a C7− hydrocarbon-containing fraction 142 and a C8 aromatic-containing fraction 143. In this case, the fraction 143 may be recycled and transferred to the xylene column 109 together with the fraction 134 discharged from the second hydrogenation unit 103.

Meanwhile, the C9+ hydrocarbon (aromatic)-containing fraction 136, which is the bottom stream of the xylene column 109, is transferred to a C9+ column 112 and split into the C9 aromatic-containing fraction 139 as the overhead stream and a C10+ aromatic-containing fraction 140 as the bottom stream. At this time, the C9 aromatic-containing fraction 139 may be combined with the fraction 128 and introduced into the transalkylation unit 107 described above.

The present disclosure will be further clearly understood with reference to the following examples. However, the following examples are provided only for illustration of the present disclosure and thus should not be construed as limiting the scope of the present disclosure.

EXAMPLES

The materials used in Examples and Comparative Examples are as follows.

ACS reagent-grade metal compounds were purchased from Sigma-Aldrich. The inorganic oxide was a commercially available product from Sigma-Aldrich. In addition, an aromatic-containing hydrocarbon fraction was obtained as a feedstock obtained through a commercial process, and a C8+ aromatic fraction having a bromine index (BI) of 655 was used.

Comparative Example 1

6 wt % Co Supported Catalyst (Reduced Form)

Cobalt nitrate was dissolved in distilled water, and the resulting solution was supported on an aluminum support by an incipient impregnation technique. Then, the resulting support was maintained at room temperature for about 1 hour and then dried at 150° C. for 2 hours in an air atmosphere and calcined at 500° C. for 2 hours. At this time, the heating rate was adjusted to 3° C./min to prepare a CoO/alumina catalyst having a Co content of 6% by weight.

40 cc of the CoO/alumina catalyst (catalyst size distribution: 20 to 40 mesh) having a Co content of 6% by weight was charged into a continuous fixed-bed reactor. Then, the atmosphere in the reactor was purged with nitrogen, and the pressure was increased to 9 kgf/cm$^2$. Thereafter, the nitrogen was replaced with hydrogen, and the temperature was raised to 450° C. while feeding hydrogen at 1,000 cc/min, followed by reduction treatment for 2 hours.

Next, the temperature in the reactor was lowered to 180° C., the flow rate of $H_2$ was adjusted to 12 cc/min, and hydrogenation was performed while feeding a C8+ aromatic fraction (BI: 655) at 1.3 cc/min. The reaction was performed for 2 days, and each obtained sample was subjected to BI measurement and gas chromatography to calculate olefin conversion and aromatic loss. The results are shown in Tables 1 and 2 below.

Comparative Example 2

6 wt % Co Supported Catalyst (Sulfide Form)

40 cc of the CoO/alumina catalyst (catalyst size distribution: 20 to 40 mesh) having a Co content of 6% by weight was charged into a continuous fixed-bed reactor. Then, the atmosphere in the reactor was purged with nitrogen and the pressure was increased to 9 kgf/cm². Thereafter, nitrogen was replaced with hydrogen, hydrogen was fed at a flow rate of 500 cc/min while toluene mixed with 2% by weight of DMDS was continuously fed at 0.7 cc/min and maintained for 5 hours, and sulfidation was performed at an elevated temperature of 350° C. for 6 hours.

Next, the temperature in the reactor was lowered to 180° C., the flow rate of $H_2$ was adjusted to 12 cc/min, and a C8+ aromatic fraction (BI: 655) was sampled and subjected to BI measurement and gas chromatography to calculate olefin conversion and aromatic loss. The results are shown in Table 1 below.

Comparative Example 3

10 wt % Mo-Supported Catalyst (Reduced Form)

Ammonium heptamolybdate was dissolved in distilled water and the resulting solution was supported on an aluminum support by an incipient impregnation technique. Then, the support was maintained at room temperature for about 1 hour and then dried at 150° C. for 2 hours in an air atmosphere and calcined at 500° C. for 2 hours. At this time, the heating rate was adjusted to 3° C./min to prepare a $MoO_3$/alumina catalyst having a Mo content of 10% by weight.

40 cc of the $MoO_3$/alumina catalyst (catalyst size distribution: 20 to 40 mesh) having a Mo content of 10% by weight was charged into a continuous fixed-bed reactor. Then, the atmosphere in the reactor was purged with nitrogen, and the pressure was increased to 9 kgf/cm². Thereafter, the nitrogen was replaced with hydrogen, and the temperature was raised to 450° C. while hydrogen was fed at 1,000 cc/min, followed by reduction treatment for 2 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography to calculate olefin conversion and aromatic loss. The results are shown in Tables 1 and 2 below.

Comparative Example 4

10 wt % Mo Supported Catalyst (Sulfide Form)

40 cc of the $MoO_3$/alumina catalyst (catalyst size distribution: 20 to 40 mesh) having a Mo content of 10% by weight was charged into a continuous fixed-bed reactor. Then, the atmosphere in the reactor was purged with nitrogen and the pressure was increased to 9 kgf/cm². Thereafter, nitrogen was replaced with hydrogen, and hydrogen was fed at a flow rate of 500 cc/min, while toluene mixed with 2% by weight of DMDS was continuously fed at 0.7 cc/min, and maintained for 5 hours, and sulfidation was performed at an elevated temperature of 350° C. for 6 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography to calculate olefin conversion and aromatic loss. The results are shown in Table 1 below.

Comparative Example 5

3 wt % Ni— and 10 wt % Mo-Supported Catalyst (Reduced Form)

Ammonium heptamolybdate was dissolved in distilled water, and the resulting solution was supported on an aluminum support by an incipient impregnation technique. Then, the resulting support was maintained at room temperature for about 1 hour and then dried at 150° C. for 2 hours in an air atmosphere and calcined at 500° C. for 2 hours. Then, nickel nitrate was dissolved in distilled water, and nickel was further supported on a molybdenum-supported aluminum support by an incipient impregnation technique. Thereafter, the resulting product was dried and calcined under the same conditions as above to prepare a $NiO$—$MoO_3$/alumina catalyst having a Ni content of 3% by weight and a Mo content of 10% by weight.

40 cc of the $NiO$—$MoO_3$/alumina catalyst (catalyst size distribution: 20 to 40 mesh) having a Ni content of 3% by weight and a Mo content of 10% by weight was charged into a continuous fixed-bed reactor. Then, the atmosphere in the reactor was purged with nitrogen, and the pressure was increased to 9 kgf/cm². Thereafter, nitrogen was replaced with hydrogen, and the temperature was raised to 450° C. while hydrogen was fed at 1,000 cc/min, followed by reduction treatment for 2 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography to calculate olefin conversion and aromatic loss. The results are shown in Table 1 below.

Comparative Example 6

3 wt % Ni— and 10 wt % Mo-Supported Catalyst (Sulfide Form)

40 cc of the $NiO$—$MoO_3$/alumina catalyst (catalyst size distribution: 20 to 40 mesh) having a Ni content of 3% by weight and a Mo content of 10% by weight was charged into a continuous fixed-bed reactor. Then, the atmosphere in the reactor was purged with nitrogen, and the pressure was increased to 9 kgf/cm². Thereafter, nitrogen was replaced with hydrogen and the hydrogen was fed at a flow rate of 500 cc/min while toluene mixed with 2% by weight of DMDS was continuously fed at 0.7 cc/min and maintained for 5 hours, and sulfidation was performed at an elevated temperature of 350° C. for 6 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography, to calculate olefin conversion and aromatic loss. The results are shown in Table 1 below.

Comparative Example 7

3 wt % Co— and 10 wt % Mo-Supported Catalyst (Reduced Form)

Ammonium heptamolybdate was dissolved in distilled water, and the resulting solution was supported on an aluminum support by an incipient impregnation technique. Then, the resulting support was maintained at room temperature for about 1 hour and then dried at 150° C. for 2 hours in an air atmosphere and calcined at 500° C. for 2 hours. Then, cobalt nitrate was dissolved in distilled water and cobalt was further supported on a molybdenum-supported aluminum support by an incipient impregnation technique. Thereafter, the resulting product was dried and calcined under the same conditions as above to prepare a $CoO$—$MoO_3$/alumina catalyst having a Co content of 3% by weight and a Mo content of 10% by weight.

40 cc of the $CoO$—$MoO_3$/alumina catalyst (catalyst size distribution: 20 to 40 mesh) having a Co content of 3% by weight and a Mo content of 10% by weight was charged into a continuous fixed-bed reactor. Then, the atmosphere in the reactor was purged with nitrogen and the pressure was increased to 9 kgf/cm². Thereafter, the nitrogen was replaced with hydrogen, and the temperature was raised to 450° C. while hydrogen was fed at 1,000 cc/min, followed by reduction treatment for 2 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, 60 days and 120 days, and each obtained sample was subjected to BI measurement and gas chromatography to calculate olefin conversion and aromatic loss. The results are shown in Tables 1 to 3 below.

Comparative Example 8

3 wt % Co— and 10 wt % Mo-Supported Catalyst (Sulfide Form)

40 cc of the $CoO$—$MoO_3$/alumina catalyst (catalyst size distribution: 20 to 40 mesh) having a Co content of 3% by weight and a Mo content of 10% by weight was charged into a continuous fixed-bed reactor. Then, the atmosphere in the reactor was purged with nitrogen, and the pressure was increased to 9 kgf/cm². Thereafter, the nitrogen was replaced with hydrogen, hydrogen was fed at a flow rate of 500 cc/min while toluene mixed with 2% by weight of DMDS was continuously fed at 0.7 cc/min and maintained for 5 hours, and sulfidation was performed at an elevated temperature of 350° C. for 6 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography to calculate olefin conversion and aromatic loss. The results are shown in Table 1 below.

Comparative Example 9

6 wt % Ni-supported catalyst (reduced form)

Nickel nitrate was dissolved in distilled water, and the resulting solution was supported on an aluminum support by an incipient impregnation method. Then, the resulting support was maintained at room temperature for about 1 hour and then dried at 150° C. for 2 hours in an air atmosphere and calcined at 500° C. for 2 hours. At this time, the heating rate was adjusted to 3° C./min.

40 cc of the NiO/alumina catalyst (catalyst size distribution: 20 to 40 mesh) having a Ni content of 6% by weight was charged into a continuous fixed-bed reactor. Then, the atmosphere in the reactor was purged with nitrogen, and the pressure was increased to 9 kgf/cm². Thereafter, the nitrogen was replaced with hydrogen, and the temperature was raised to 450° C. while hydrogen was fed at 500 cc/min, followed by reduction treatment for 2 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography to calculate olefin conversion and aromatic loss. The results are shown in Table 1 below.

Comparative Example 10

6 wt % Ni-Supported Catalyst (Sulfide Form)

40 cc of the NiO/alumina catalyst (catalyst size distribution: 20 to 40 mesh) having a Ni content of 6% by weight was charged into a continuous fixed-bed reactor. Then, the atmosphere in the reactor was purged with nitrogen, and the pressure was increased to 9 kgf/cm². Thereafter, the nitrogen was replaced with hydrogen, the hydrogen was fed at a flow rate of 500 cc/min, while toluene mixed with 2% by weight of DMDS was continuously fed at 0.7 cc/min and maintained for 5 hours, and sulfidation was performed at an elevated temperature of 350° C. for 6 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography, to calculate olefin conversion and aromatic loss. The results are shown in Table 1 below.

Comparative Example 11

3 wt % Pd-Supported Catalyst (Reduced Form)

Palladium chloride was dissolved in distilled water, and the resulting solution was supported on an aluminum support by an incipient impregnation technique. Then, the resulting support was maintained at room temperature for about 1 hour and then dried at 150° C. for 2 hours in an air atmosphere and calcined at 500° C. for 2 hours. At this time, the heating rate was adjusted to 3° C./min to prepare a PdO/alumina catalyst having a Pd content of 3% by weight.

40 cc of the PdO/alumina catalyst (catalyst size distribution: 20 to 40 mesh) having a Pd content of 3% by weight was charged into a continuous fixed-bed reactor. Then, the atmosphere in the reactor was purged with nitrogen, and the pressure was increased to 9 kgf/cm². Thereafter, the nitrogen was replaced with hydrogen, and the temperature was raised to 450° C. while hydrogen was fed at 1,000 cc/min, followed by reduction treatment for 2 hours.

Next, the temperature in the reactor was lowered to 180° C., the flow rate of $H_2$ was adjusted to 12 cc/min, and hydrogenation was performed while a C8+ aromatic fraction (BI: 655) was fed at 1.3 cc/min. The reaction was performed for 2 days, and each obtained sample was subjected to BI measurement and gas chromatography to calculate olefin conversion and aromatic loss. The results are shown in Table 1 below.

Comparative Example 12

Hydrogenation was performed in the same manner as in Comparative Example 1, except that the hydrogenation was performed for 30 days, and the results are shown in Table 2 below.

Comparative Example 13

Hydrogenation was performed in the same manner as in Comparative Example 3, except that the hydrogenation was performed for 30 days, and the results are shown in Table 2 below.

Comparative Example 14

Hydrogenation was performed in the same manner as in Comparative Example 7, except that the hydrogenation was performed for 30 days and 60 days, and the results are shown in Table 2 below.

sulfide-type catalyst (Comparative Example 6), CoMo sulfide-type catalyst (Comparative Example 8), and Ni sulfide-type catalyst (Comparative Example 10) exhibited relatively low olefin conversion, in other words, relatively low olefin removal efficiency of 77.1%, 71.0%, 73.7%, 75.6%, and 56.8%, respectively, but effectively suppressed aromatic loss.

The reduced-type Co catalyst (Comparative Example 1), reduced-type Mo catalyst (Comparative Example 3), reduced-type NiMo catalyst (Comparative Example 5), and reduced-type CoMo catalyst (Comparative Example 7) exhibited good olefin conversion, i.e., olefin removal efficiency, of 91.1%, 87.2%, 90.4%, and 96.2%, respectively, and suppressed aromatic loss, except for the reduced-type NiMo catalyst. In particular, the reduced-type NiMo catalyst exhibited the high aromatic loss of 1.23%.

Meanwhile, as can be seen from Table 2, the reduced-type Co catalyst (Comparative Example 12), reduced-type Mo catalyst (Comparative Example 13), and reduced-type CoMo catalyst (Comparative Example 14) exhibited a sharp decrease in olefin conversion as the reaction time increased. Upon application to a commercial process, this tendency toward decreased durability increases the cost of catalyst

TABLE 1

| | Comparative Example | | | | | | | | | | |
|---|---|---|---|---|---|---|---|---|---|---|---|
| | 1 | 2 | 3 | 4 | 5 | 6 | 7 | 8 | 9 | 10 | 11 |
| | Catalyst | | | | | | | | | | |
| | Co (reduced) | Co (sulfide) | Mo (reduced) | Mo (sulfide) | NiMo (reduced) | NiMo (sulfide) | CoMo (reduced) | COMo (sulfide) | Ni (reduced) | Ni (sulfide) | Pd (reduced) |
| Olefin Conversion (%) | 91.1 | 77.1 | 87.2 | 71.0 | 90.4 | 73.7 | 96.2 | 75.6 | 80.2 | 56.8 | 74.0 |
| Aromatic Loss (%) | 0.04 | 0.03 | 0.03 | 0.03 | 1.23 | 0.04 | 0.04 | 0.04 | 1.37 | 0.03 | 1.34 |

TABLE 2

| | Comparative Example | | | | | | |
|---|---|---|---|---|---|---|---|
| | 12 | | 13 | | 14 | | |
| | Catalyst | | | | | | |
| | Co (reduced) | | Mo (reduced) | | CoMo (reduced) | | |
| DOS[1] | 2 | 30 | 2 | 30 | 2 | 30 | 60 |
| Olefin Conversion (%) | 91.1 | 74.0 | 87.2 | 77.1 | 96.2 | 92.4 | 87.8 |
| Aromatic Loss (%) | 0.04 | 0.03 | 0.04 | 0.03 | 0.04 | 0.04 | 0.03 |

[1]days on stream

As can be seen from Table 1, hydrogenation was performed using each of the reduced-type Ni catalyst (Comparative Example 9) and the reduced-type Pd catalyst (Comparative Example 11) at a temperature of 180° C. As a result, the reduced-type Ni catalyst and the reduced-type Pd catalyst exhibited product-olefin conversion of 80.2% and 74.0%, respectively, but very high aromatic loss higher than 1.34%. It is supposed that application of each of the reduced-type Ni catalyst and the reduced-type Pd catalyst to a commercial process, which involves the same reaction and similar operating conditions, reduces the amount of aromatic production and thus results in economic loss.

[1]: days on stream

The Co sulfide-type catalyst (Comparative Example 2), Mo sulfide-type catalyst (Comparative Example 4), NiMo replacement and requires frequent catalyst replacement, and thus is expected to adversely affect process efficiency.

Comparative Example 15

20 cc of the NiMo-supported catalyst (reduced form) according to Comparative Example 5 and 20 cc of the CoMo-supported catalyst (reduced form) according to Comparative Example 7 were sequentially charged into a continuous fixed-bed reactor, hydrogenation was performed in the same manner as in Comparative Example 1, and the results are shown in Table 3 below.

Comparative Example 16

20 cc of the CoMo-supported catalyst (reduced form) according to Comparative Example 7 and 20 cc of the Ni-supported catalyst (reduced form) according to Comparative Example 9 were sequentially charged into a continuous fixed-bed reactor, hydrogenation was performed in the same manner as in Comparative Example 1, and the results are shown in Table 3 below.

Comparative Example 17

20 cc of the CoMo-supported catalyst (reduced form) according to Comparative Example 7 and 20 cc of the Pd-supported catalyst (reduced form) according to Comparative Example 11 were sequentially charged into a continuous fixed-bed reactor, hydrogenation was performed in the same manner as in Comparative Example 1, and the results are shown in Table 3 below.

Example 1

20 cc of the CoMo-supported catalyst (reduced form) according to Comparative Example 7 and 20 cc of the NiMo-supported catalyst (reduced form) according to Comparative Example 5 were sequentially charged into a continuous fixed-bed reactor, hydrogenation was performed in the same manner as in Comparative Example 1, and the results are shown in Table 3 below.

Example 2

20 cc of the Mo-supported catalyst (reduced form) according to Comparative Example 3 and 20 cc of the NiMo-supported catalyst (reduced form) according to Comparative Example 5 were sequentially charged into a continuous fixed-bed reactor, hydrogenation was performed in the same manner as in Comparative Example 1, and the results are shown in Table 3 below.

Example 3

Two reactors were used, and in each of the reactors, catalyst pretreatment was independently performed. 20 cc of the NiMo-supported catalyst was charged into the first reactor, and then sulfidation was performed in the same manner as in Comparative Example 6, and in the second reactor, 20 cc of the NiMo-supported catalyst was charged, and then reduction treatment was performed in the same manner as in Comparative Example 5. The two reactors independently pretreated in this way were sequentially connected in series, hydrogenation was performed in the same manner as in Comparative Example 1, and the results are shown in Table 4 below.

TABLE 4

| Item | Example 3 | |
| --- | --- | --- |
| 1$^{st}$ Reactor | NiMo (sulfide) | |
| 2$^{nd}$ Reactor | NiMo (reduced) | |
| DOS | 2 | 30 |
| Olefin Conversion (%) | 93.6 | 92.1 |
| Aromatic Loss (%) | 0.04 | 0.03 |

As can be seen from Table 3, when the NiMo-supported catalyst (reduced form) is charged in the first bed and the CoMo-supported catalyst (reduced form) is charged in the second bed (Comparative Example 15), the olefin conversion of hydrogenated products and loss of aromatics were substantially similar to those of Comparative Example 5 using the NiMo supported catalyst (reduced form). On the other hand, Example 1, in which the CoMo-supported catalyst (reduced form) was charged in the first bed and the NiMo-supported catalyst (reduced form) was charged in the second bed, showed a very high olefin conversion of the hydrogenated product and remarkably reduced aromatic loss compared to Comparative Examples 6 and 15.

Further, Example 2 exhibited an improved olefin reduction, and in particular, significantly improved durability, compared to Comparative Example 13.

In addition, Example 3 showed an olefin conversion of 93.6%, which was greatly increased than the olefin conversion of 73.7% for Comparative Example 6, in which only the NiMo-supported catalyst (sulfide form) was charged. Even after hydrogenation was performed for 30 days, the olefin conversion slightly decreased to 92.1%, which indicates that olefin was effectively decreased when compared to 73.7% of the olefin conversion obtained through hydrogenation for 2 days in Comparative Example 6.

Example 4

5 cc of the CoMo-supported catalyst (reduced form) according to Comparative Example 7 and 35 cc of the NiMo-supported catalyst (reduced form) according to Comparative Example 5 were sequentially charged into a continuous fixed-bed reactor, hydrogenation was performed in the same manner as in Comparative Example 1, and the results are shown in Table 5 below.

Example 5

10 cc of the CoMo-supported catalyst (reduced form) according to Comparative Example 7 and 30 cc of the NiMo-supported catalyst (reduced form) according to Comparative Example 5 were sequentially charged into a continuous fixed-bed reactor, hydrogenation was performed in the same manner as in Comparative Example 1, and the results are shown in Table 5 below.

TABLE 3

| Item | Comparative Example 15 | Comparative Example 16 | Comparative Example 17 | Example 1 | | | Example 2 | |
| --- | --- | --- | --- | --- | --- | --- | --- | --- |
| 1$^{st}$ Bed | NiMo (reduced) | CoMo (reduced) | CoMo (reduced) | CoMo (reduced) | | | Mo (reduced) | |
| 2$^{nd}$ Bed | CoMo (reduced) | Ni (reduced) | Pd (reduced) | NiMo (reduced) | | | NiMo (reduced) | |
| DOS | 2 | 2 | 2 | 2 | 30 | 60 | 2 | 30 |
| Olefin Conversion (%) | 90.1 | 95.1 | 94.7 | 96.6 | 95.4 | 95.1 | 91.0 | 92.2 |
| Aromatic Loss (%) | 1.12 | 1.21 | 1.22 | 0.04 | 0.04 | 0.03 | 0.04 | 0.03 |

Example 6

30 cc of the CoMo-supported catalyst (reduced form) according to Comparative Example 7 and 10 cc of the NiMo-supported catalyst (reduced form) according to Comparative Example 5 were sequentially charged into a continuous fixed-bed reactor, hydrogenation was performed in the same manner as in Comparative Example 1, and the results are shown in Table 5 below.

Example 7

35 cc of the CoMo-supported catalyst (reduced form) according to Comparative Example 7 and 5 cc of the NiMo-supported catalyst (reduced form) according to Comparative Example 5 were sequentially charged into a continuous fixed-bed reactor, hydrogenation was performed in the same manner as in Comparative Example 1, and the results are shown in Table 5 below.

TABLE 5

| Example | 4 | 5 | 3 | 6 | 7 |
|---|---|---|---|---|---|
| CoMo (reduced) (cc) | 5 | 10 | 20 | 30 | 35 |
| NiMo (reduced) (cc) | 35 | 30 | 20 | 10 | 5 |
| DOS | 2 | 2 | 2 | 2 | 2 |
| Olefin Conversion (%) | 96.2 | 96.9 | 96.6 | 95.9 | 95.6 |
| Aromatic Loss (%) | 0.07 | 0.05 | 0.04 | 0.04 | 0.04 |

As can be seen from Table 5, as a result of the experiment performed while changing the volume ratio between the reduced-type CoMo catalyst and the reduced-type NiMo catalyst, the aromatic loss slightly increased as the content of the reduced-type NiMo catalyst increased, but the olefin removal rate was remarkably improved, and the aromatic loss was also low compared to Comparative Example 6, in which the reduced-type NiMo catalyst was used alone.

Comparative Example 18

In the same manner as in Comparative Example 5, 10 cc of a NiMo supported catalyst (reduced form) was charged into the reactor, for hydrogenation, the pressure was adjusted to 15 bar, the temperature was adjusted to 100° C., and an $H_2$ flow rate was adjusted to 30 cc/min, and hydrogenation was performed while feeding a hydrocarbon fraction containing 13.6% by weight of benzene and 49.6% by weight of toluene, and further containing 1.5% by weight of olefin at a flow rate of 1.3 cc/min. The results are shown in Table 6 below.

Example 8

Hydrogenation was performed in the same manner as in Comparative Example 18, except that 8 cc of the CoMo-supported catalyst (reduced form) according to Comparative Example 7 (the upper portion of the reactor), and 2 cc of the NiMo-supported catalyst (reduced form) according to Comparative Example 5 (the lower portion of the reactor) were sequentially charged into a continuous fixed-bed reactor, and the results are shown in Table 6 below.

TABLE 6

| Item | Comparative Example 18 | Example 8 |
|---|---|---|
| CoMo (reduced) (cc) | 0 | 8 |
| NiMo (reduced) (cc) | 10 | 2 |
| DOS | 2 | 2 |
| Olefin Conversion (%) | 99 | 99.2 |
| Aromatic Loss (%) | 1.5 | 0.05 |

As can be seen from Table 6, Example 8, in which different types of catalysts having different active metals were charged in a staged loading manner, showed a similar olefin conversion, but effectively suppressed aromatic loss, compared to Comparative Example 18 using the NiMo supported catalyst (reduced form) alone.

In addition, the BI of the products over time using the CoMo supported catalyst (reduced form) used in Comparative Example 7 alone, and a catalyst system, in which two catalysts ((CoMo-supported catalyst (reduced form) and NiMo-supported catalyst (reduced form)) are charged in a staged loading manner, was measured, and an olefin conversion was calculated. The results are shown in FIG. 4.

Figure 4:
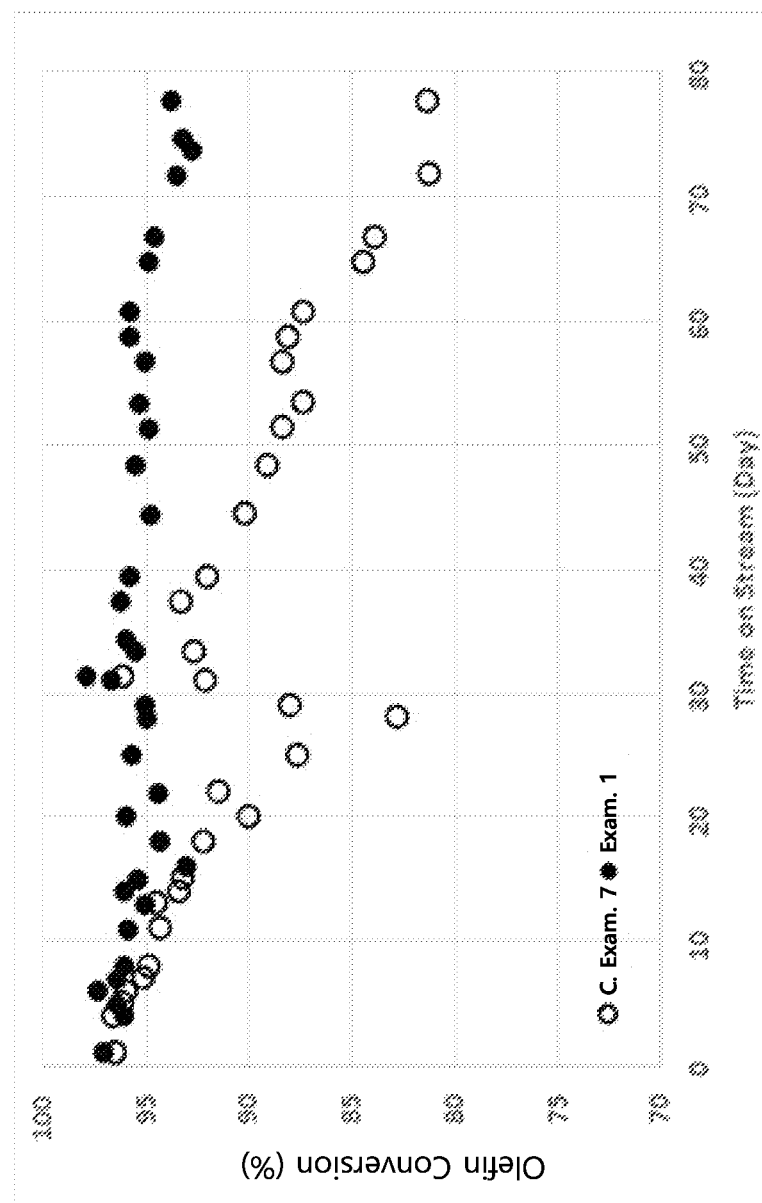
FIG. 4 is a graph showing the change in the bromine index (BI) of the product over reaction time during the hydrogenation according to Comparative Example 7 and Example 1.

As can be seen from FIG. 4, the durability of the catalyst system was greatly improved when the two catalysts were charged in a staged loading manner in a specific order.

As is apparent from the above description, according to an embodiment of the present disclosure, the unsaturated hydrocarbons contained in the aromatic hydrocarbon fraction can be removed through selective hydrogenation, aromatic loss can be suppressed, and excellent selective hydrogenation activity can be maintained even during long-term operation by employing catalyst beds through staged loading of a plurality of hydrogenation catalysts having different catalytic properties, or by employing a catalyst system in which a plurality of hydrogenation catalysts are arranged to be equivalent to the staged loading by use of a plurality of reactors. As a result, the catalyst and catalyst system according to the disclosure are capable of improving process efficiency, such as reducing aromatic loss during selective hydrogenation to realize stable operation, compared to the conventional catalysts or catalyst systems, and thus are expected to be widely commercialized in the future.

Although the preferred embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed is:

1. A method of removing unsaturated hydrocarbons in an aromatic fraction, which comprises:
   a) providing an aromatic hydrocarbon-containing feedstock having a bromine index of 30 to 15,000, and
   b) bringing the feedstock into contact with a multi-stage catalyst bed comprising at least one first catalyst bed and a second catalyst bed disposed downstream of the at least one first catalyst bed in a reactor and performing hydrogenation in a liquid phase reaction or three-phase reaction under supply of hydrogen to form an aromatic hydrocarbon-containing product having a reduced bromine index,
   wherein,
   the at least one first catalyst bed comprises a support containing inorganic oxide, and at least one active metal selected from the group consisting of Ni, Pd, Pt, Ru, Re, Co, Mo, Co—Mo, Ni—Mo, and Ni—W, in which, among the active metals, each of Re, Co, Mo, and Co—Mo is a reduced or sulfide form, and each of Ni, Pd, Pt, Ru, Ni—Mo and Ni—W is a sulfide form, the second catalyst bed comprises a support containing inorganic oxide, and Ni—Mo and/or Ni—W in a reduced form as an active metal, the at least one first catalyst bed exhibits a less activity for aromatic loss than the second catalyst bed, and hydrogen supplied on the at least one first catalyst bed is consumed as the hydrogenation proceeds such that hydrogen is supplied on the second catalyst bed in an amount lower than on the at least one first catalyst bed, and a temperature of the hydrogenation is determined within a range from room temperature to less than 230° C.

2. A method of removing unsaturated hydrocarbons in an aromatic fraction, which comprises:
 a) providing an aromatic hydrocarbon-containing feedstock having a bromine index of 30 to 15,000, and
 b) transferring the feedstock to a multi-stage hydrogenation unit comprising a first reaction unit containing at least one first catalyst and a second reaction unit containing a second catalyst and communicating with the first reaction unit at the downstream of the first reaction unit and performing hydrogenation in a liquid phase reaction or three-phase reaction under supply of hydrogen to form an aromatic hydrocarbon-containing product having a reduced bromine index,
wherein,
 the at least one first catalyst comprises a support containing inorganic oxide, and at least one active metal selected from the group consisting of Ni, Pd, Pt, Ru, Re, Co, Mo, Co—Mo, Ni—Mo, and Ni—W, in which, among the active metals, each of Re, Co, Mo, and Co—Mo is a reduced or sulfide form, and each of Ni, Pd, Pt, Ru, Ni—Mo and Ni—W is a sulfide form,
 the second catalyst comprises a support containing inorganic oxide, and Ni—Mo and/or Ni—W in a reduced form as an active metal,
 the at least one first catalyst exhibits a less activity for aromatic loss than the second catalyst, and
 hydrogen supplied to the first reaction unit is consumed as the hydrogenation proceeds such that hydrogen is supplied to the second reaction unit in an amount lower than the first reaction unit, and
 a temperature of the hydrogenation is determined within a range from room temperature to less than 230° C.

3. The method according to claim 1, wherein at least 30% by weight of unsaturated hydrocarbons in the aromatic hydrocarbon-containing feedstock is removed by hydrogenation.

4. The method according to claim 1, wherein an aromatic loss in the aromatic hydrocarbon-containing product is less than 1% by weight relative to the aromatic hydrocarbon-containing feedstock.

5. The method according to claim 2, wherein the first reaction unit comprises a plurality of reactors connected in series.

6. The method according to claim 1, wherein an amount of hydrogen supplied to the hydrogenation is within a range of at least 0.5 moles with respect to 1 mole of unsaturated hydrocarbons present in the feedstock.

7. The method according to claim 1, wherein a pressure for the hydrogenation is determined within a range of 3 to 70 bar.

8. The method according to claim 1, wherein the inorganic oxide comprises at least one selected from the group consisting of alumina, silica, silica-alumina, aluminum phosphate, zirconia, titania, bentonite, kaolin, clinoptilolite and montmorillonite.

9. The method according to claim 1, wherein a content of the active metal in the first catalyst ranges from 0.5 to 40% by weight, and a content of the active metal in the second catalyst ranges from 2 to 40% by weight.

10. The method according to claim 1, wherein the aromatic hydrocarbon-containing feedstock has a boiling point in a range of 35 to 300° C.

11. The method according to claim 1, wherein the aromatic hydrocarbon-containing feedstock is a C5+ reformate.

12. The method according to claim 1, wherein an amount of the at least one first catalyst bed is in a range of 10 to 90%, based on the total volume of the at least one first catalyst bed and the second catalyst bed.

13. The method according to claim 1, wherein the aromatic hydrocarbon-containing feedstock contains C6 to C18 alkyl aromatic hydrocarbons.

14. The method according to claim 13, wherein the aromatic hydrocarbon-containing feedstock contains benzene, toluene, xylene, and/or C9+ aromatics.

15. The method according to claim 1, wherein an aromatic content of the aromatic hydrocarbon-containing feedstock is in a range of at least 50% by weight.

16. The method according to claim 1, wherein the support in each of the at least one first catalyst bed and the second catalyst bed is in a shape of cylinder, granule, pellet, tablet or sphere.

17. The method according to claim 1, wherein the support in each of the at least one first catalyst bed and the second catalyst bed exhibits an apparent density of 0.3 to 1.2 g/cc, an average pore diameter of 3 to 1,000 nm, and a specific surface area (BET) of 10 to 1,000 m$^2$/g.

18. The method according to claim 7, wherein a space velocity (LHSV) of the aromatic-containing feedstock is controlled within a range of 0.3 to 30 hr$^{-1}$.

19. The method according to claim 1, which further comprises subjecting the aromatic hydrocarbon-containing product having a reduced bromine index to benzene, toluene or xylene product separation, transalkylation, or xylene isomerization.

* * * * *